United States Patent [19]
Savic

[11] Patent Number: 5,327,893
[45] Date of Patent: Jul. 12, 1994

[54] DETECTION OF CHOLESTEROL DEPOSITS IN ARTERIES

[75] Inventor: Michael Savic, Ballston Lake, N.Y.

[73] Assignee: Rensselaer Polytechnic Institute, Troy, N.Y.

[21] Appl. No.: 962,777

[22] Filed: Oct. 19, 1992

[51] Int. Cl.$^5$ .............................................. A61B 8/00
[52] U.S. Cl. ............................................... 128/661.08
[58] Field of Search ...................... 128/661.07–661.10; 73/861.25

[56] References Cited

U.S. PATENT DOCUMENTS 4,719,923  1/1988  Hartwell et al. ............... 128/661.08
4,770,184  9/1988  Greene, Jr. et al. ........... 128/661.08

OTHER PUBLICATIONS

Langlois, Y. et al "Evaluating Carotid Artery Disease", Ultrasound in Medicine & Biology, vol. 9 #1, pp. 51–63, 1983.

*Primary Examiner*—Francis Jaworski
*Attorney, Agent, or Firm*—Notaro & Michalos

[57] ABSTRACT

A method of diagnosing arterial stenosis from a received Doppler shifted acoustic signal from an artery during multiple heartbeats, each having systolic and diastolic phases uses pattern recognition techniques that are applied to the signal to determine the presence of turbulence during the diastolic phases which indicates stenosis. This is advantageously done by comparing the systolic and diastolic phases as part of the pattern recognition technique, large differences being indicative of a healthy artery and smaller differences being indicative of stenosis.

14 Claims, 9 Drawing Sheets

NORMAL ARTERY

STENOTIC ARTERY

FIG. II

DETECTION OF CHOLESTEROL DEPOSITS IN ARTERIES

FIELD AND BACKGROUND OF THE INVENTION

The present invention relates in general to cardiovascular diagnosis techniques, and in particular to a new, simple, inexpensive yet accurate system for the diagnosis of arterial stenosis, that is, cholesterol deposits in the carotid artery.

The carotid artery is the artery that carries blood from the heart to the brain. Carotid arterial stenosis is a cerebrovascular disease that is caused by cholesterol deposits inside the artery. These deposits clog the artery and prevent the normal flow of blood. During the systolic cycle, the heart pumps blood into the arterial system, the velocity of blood is high, and the flow of blood is turbulent even if there is no stenosis. If the artery is "clean" there is no turbulence inside the artery during the diastolic cycle when the heart does not pump and when blood flows slowly in the opposite direction due to the elasticity of the arterial system. However, if there are deposits inside the carotid artery (stenosis) the flow of blood will be turbulent even during the diastolic cycle.

The "Doppler frequency-shift effect" was predicted by the astronomer Christian Doppler in 1842 and was experimentally confirmed in 1845. It was 30 years after ultrasound had been used in the military to detect submarines, that the first practical ultrasonic Doppler device for use in medicine was designed and constructed by Satomura in 1956.

Three decades later, there has been a widespread expansion of Doppler ultrasonic applications into virtually all areas of cardiovascular diagnostics.

According to the Doppler effect, a reflected frequency from a moving object will be shifted from the original transmitted frequency. The arterial Doppler signal is formed as follows: an ultrasonic transducer is placed in contact with the skin surface, and the ultrasound beam whose frequency is $f_o$ is directed toward the blood vessel. The source of the echo signals are the red blood cells flowing in the vessel. The reflected signal frequency is denoted as $f_r$. The Doppler frequency shift, $f_D$, will be related to the velocity of the reflector, v, by the equation, $$f_D = (2f_o v/c) \cos \Theta \qquad (1)$$

where c is the speed of sound and $\Theta$ is the angle between the direction of the blood flow and the ultrasonic beam. It can been seen that $f_D$ will change along with changing $\Theta$. When $\Theta = 90°$, $\cos \Theta = 0$, which is an undesirable situation because no Doppler shift will be detected. In practice, the transducer is usually oriented and fixed to make a 30°-60° angle with the arterial lumen to ensure the correct measurement of v.

Since all reflectors flowing at different speeds within the sound beam are contributing to the Doppler frequency shift, $f_r$, the output $f_D$ is a complex signal occupying a wide frequency range.

Whenever an ultrasound beam strikes an interface formed by two tissues having different acoustic properties, part of the beam is reflected and part is transmitted. If the reflected wave travels back toward the ultrasound source, it may be detected as an echo. The amplitude of the reflected wave is determined by the different in acoustic impedances of the material forming the interface.

The acoustic impedance, Z, is the speed of sound in a material multiplied by its density. For a perpendicular angle of incidence of an ultrasound beam on a large, flat interface, the ratio of the reflected to the incident amplitude, R, is given by $$R = (Z_2 - Z_1)/(Z_2 + Z_1) \qquad (2)$$

where $Z_1$ is the impedance of the substance in which the reflected beam will travel, and $Z_2$ is the impedance of the substance in which the incident beam travels. Equation (2) shows that the larger the difference between $Z_1$ and $Z_2$, the more energy is reflected and the greater is the echo.

Despite the existence of Doppler effect techniques used for measuring the acoustic properties of living tissues, a need remains for a simple reproducible, non-invasive technique for detecting when and how much cholesterol has deposited in an individual's arteries.

SUMMARY OF THE INVENTION

According to the present invention, a 5 MHz ultrasonic beam is directed from a transmitting transducer toward an artery to be examined. The signal reflected from the bloodstream is received by another transducer. Due to the Doppler effect, the received signal contains a low frequency component that is within audible range.

Features of this low frequency signal such as the linear predictive coefficients or the LPC cepstrum coefficients contain information about turbulence in the artery, and thus information about deposits inside the artery.

The energy of the Doppler signal can also be used as an indicator of stenosis, since this energy is high when turbulence in the artery is present. Accordingly, a high energy Doppler signal in the diastolic cycle indicates stenosis. As a result, larger variations of energy between the systolic and diastolic cycles occur for a healthy person, than for a patient with stenosis.

An autocorrelation analysis in the time domain has also been performed on the Doppler signal according to the invention. The results show distinct differences between signals from patients with and without stenosis. There is a much higher correlation between the signals taken during diastolic and systolic cycles for a patient with stenosis, than for a healthy patient.

The behavior of the Doppler signal in the frequency domain has also been studied. The signal is cyclo-stationary, alternating between two states. The "two-state" stationarity assumes that the signal within the systole is stationary, implying that signal values are drawn from the same probability distribution. The same holds for the diastole. This assumption was experimentally verified by performing a short time Fourier transformation. For all frames taken for diastole, the obtained spectrum was similar, which means that the process is wide-sense stationary. Feature vectors obtained from different frames within the same diastole (or systole) are assumed to observe the same statistical distribution. This assumption was used as the basis for feature extraction and pattern recognition that can be used to detect the cholesterol deposits.

An additional objective of the present invention is to extract dominant features from the Doppler signal and use these features to determine the degree of stenosis. A method based on dominant feature selection using the Hotelling trace criterion was utilized. The LPC cepstrum coefficients were used as features, with good results. A Gaussian distribution was assumed for the feature vector. The mean and covariance were estimated from the entire training data set. A quadratic classifier was implemented and the resulting distribution of the likelihood ratio (classification score) was plotted. This plot shows good separation of scores for different classes. The determination of the degree of stenosis can be made by using a simple threshold comparator. A quadratic classifier gives a reliable diagnosis even if only a single frame of data is used. In a preferred embodiment of the invention, the observations were much longer, and consistent of about 100 usable feature vectors in a 5 second interval. Significant improvement in performance is obtained when the Wald sequential test was used. The combination of a quadratic classifier and the Wald sequential test yielded a final classification error of less than 5%.

Accordingly, an object of the present invention is to provide a method of diagnosing arterial stenosis comprising: detecting an acoustic signal from an artery; digitizing the acoustic signal to form a digital signal on which computational analysis can be performed; and subjecting the digital signal to pattern recognition analysis to distinguish digital signals of an artery with stenosis from digital signals of a normal artery.

In more detail, an object of the present invention is to provide a method of diagnosing arterial stenosis, which subjects the digital signal to pattern recognition analysis by extracting or selecting dominant features for stenosis, from the acoustic signal, using a discriminant analysis disclosed in the present application, the selected features being multidimensional in a feature space, thereafter projecting the multidimensional feature space into the best directions for analysis, for example, autocorrleating a Doppler acoustic signal in the time domain, or plotting a power spectrum of the Doppler signal in the frequency domain, and further, after the projection step, classifying the results to indicate whether stenosis exists or not, for example by analyzing the power spectrum to determine whether it is weighted toward a low frequency end of the spectrum, which would indicate stenosis.

A further object of the present invention is to provide an apparatus for diagnosing arterial stenosis which relies on the pattern recognition techniques of which the present invention.

A still further object of the present invention is to provide a medical diagnostic technique for arterial stenosis which is non-invasive yet rapid and accurate.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

DESCRIPTION OF THE PREFERRED EMBODIMENTS

The task of diagnosis is basically to recognize whether the signal indicates stenosis nor not. The diagnosing problem is a practical implementation of pattern recognition techniques. Pattern recognition is defined as machine interpretation of patterns. Statistical pattern recognition usually consists of estimating probability density functions in a high-dimensional space and dividing the space into regions of categories.

In the present invention, ultrasonic Doppler signal equipment is used with an analog-to-digital converter to interface between a patient and a computer. The computer is used to extract useful information from the signals by reducing the signals to features which can undergo classification.

Feature selection and extraction is generally considered the most important and complex task of pattern recognition. The goal is to produce clusters which are separated in a feature space. The "separability" of the various pattern classes can be enhanced by adding more features or selecting more representative features.

By adding features, the feature space is increased dimensionally and, therefore, this tends to complicate the recognition problem both analytically and computationally. Therefore, the present invention concentrates on the second alternative.

According to the invention, an acoustic signal is either stenotic or normal. Features which will exhibit a high variation between normal and stenotic signals are thus needed. That is, the signal should be stenosis-dependent. Also, since we want to diagnose stenosis on different patients with a large variation of physical and health conditions, we want the features to be patient-independent.

According to the present invention, time and frequency domain analysis of a Doppler signal coming from a patient's arteries, is related to the patients stenotic condition. As will be explained later, pattern recognition according to the present invention utilizes LPC cepstrum coefficients as features, which are being classified in a classifier in order to evaluate the degree of stenosis. For a more complete mathematical disclosure of LPC cepstrum analysis and its application to pattern recognition in audio signals, please refer to a co-pending U.S. patent application Ser. No. 07/959,143, to the inventor of the present application, entitled DETECTION OF LEAKS IN PIPELINES, which is incorporated here by reference.

Figure 1:
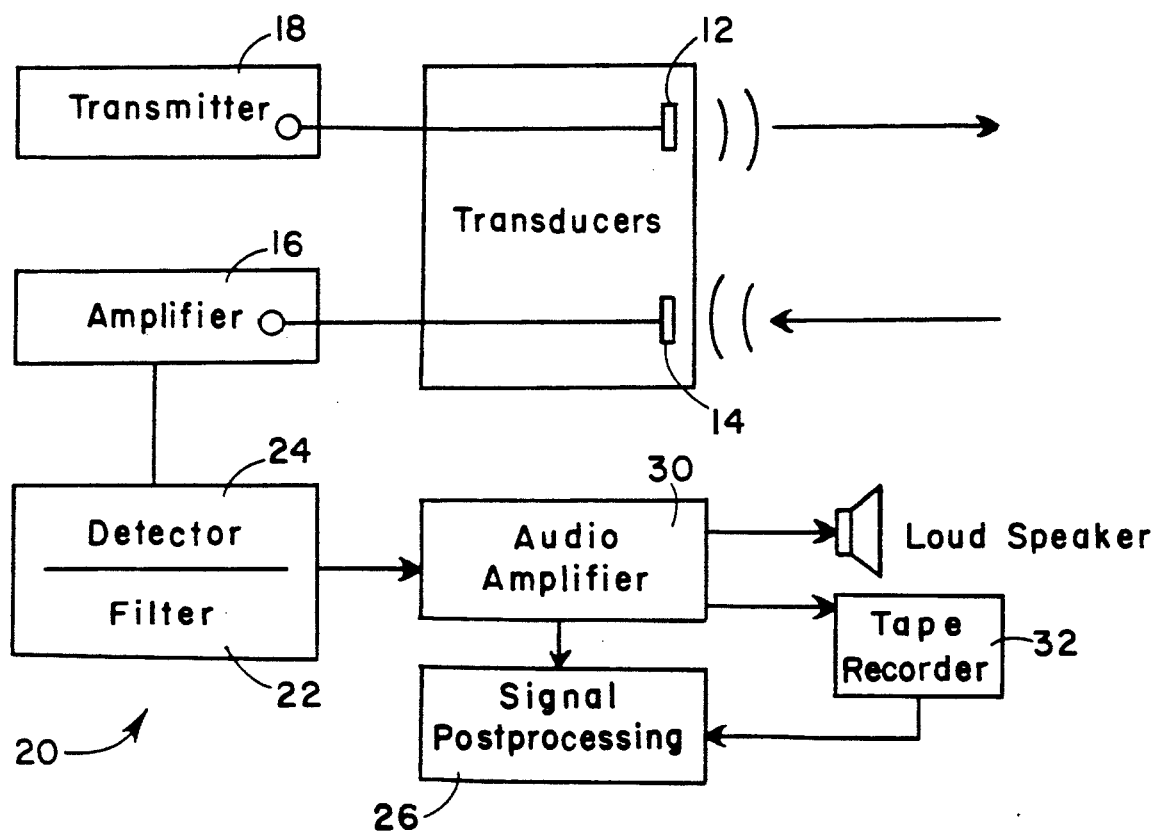
FIG. 1 is a schematic block diagram showing a continuous wave Doppler instrument which can be used to practice the present invention.

There are two main designs for an ultrasonic Doppler device: continuous-wave Doppler and pulsed Doppler. The continuous-wave method is the least expensive Doppler device and is shown in FIG. 1. It uses two ultrasonic crystals 12, 14, that are used as transducers, matched in natural frequency and positioned such that one transducer 12 constantly sends out an ultrasonic beam supplied to it by transmitter 18, and the other transducer 14 receives the echoes or reflected waves, amplifies the received signal at 16, and passes the signal on to processing circuitry 20 for Doppler frequency-shift extraction in a signal processor 26. When studying Doppler signals due to blood flow, relatively low frequency signals originating from the movement of vessel walls and detected at detector 24 may be eliminated by a high-pass filter 22.

A pulse-Doppler transducer consists of only a single crystal serving both as the transmitter and receiver. By adjusting the delay between reception and transmission, one can discriminate the Doppler signals from different depths, allowing for the detection of moving reflectors within a well-defined "sample volume", that is the patient's body. Pulsed Doppler also has the advantage of perfect matching between the frequencies of the sending and receiving crystals. With either type of device, the detected and filtered signals are amplified again at 30 and may also be recorded in a tape recorder 32.

With a pulsed Doppler instrument a performance limitation occurs related to the pulse repetition frequency (PRF) of the instrument and the maximum frequency of the Doppler signal that can be correctly measured. From the sampling theorem, we know that to prevent aliasing of a Doppler signal whose frequency is $f'_D$, the pulse repetition frequency must be at least twice $f'_D$, that is, $PRF \geq 2f'_D$. On the other hand, an upper limit on the pulse repetition frequency is established by the time interval required for ultrasonic pulses to propagate to the range of interest and return. The time, T, for a pulse to travel a distance d and return to the transducer is given by $$T = 2d/c \quad (3)$$

where c is the speed of sound in the medium. The inverse of T, 1/T, is the maximum PRF allowable for detecting signals from reflectors at the depth d.

Another important issue is the selection of the right ultrasound frequency. Comparing Eq. (3) with Eq. (1), the relation between the maximum velocity and the proper ultrasound frequency (assume $\Theta = 0°$) is:

$$V_{max} = c^2/8f_0 d \quad (4)$$

The speed of sound in biological tissue varies from 1450 m/sec in fat to 1620 m/sec in the lens tissue of eyes. Depending upon the depth of the artery, a suitable ultrasound frequency is selected according to Eq. (4).

In practical application, the Doppler frequency system is usually used in conjunction with an ultrasonic scanner, called B-mode (brightness-mode) scanning.

The position and orientation of the incident ultrasound beam, along with the echo return time, are used to place echo signals in their representative anatomical positions on the display. The intensities are determined by the strength of the reflected signal, which is characteristic of tissues that served as reflectors. The scanner and a Doppler instrument provide complementary information in that the scanner can show the outline of anatomical structures, whereas, a Doppler instrument yields information regarding flow and movement patterns. "Duplex" ultrasound instruments are real-time B-mode scanners with built-in Doppler capabilities. Typically, the B-mode image is used to help localize areas where flow will be examined using Doppler. The area to be studied in the Doppler signal may be identified on the B-mode image with a "sample volume indicator". The indicator position is controlled by the operator, greatly facilitating positioning the Doppler sample volume over the region of interest. After the Doppler signal from the area of interest is obtained, various signal analyses are performed to decide if the artery has stenosis or not. The invention includes a new approach for feature extraction and pattern classification on the Doppler signal in order to achieve automatic diagnosis of arterial stenosis.

The B-mode ultrasonic scanner is used to help locate and direct the ultrasonic beam to insure the right "sample volume", while the actual flow pattern information is contained in the Doppler signal produced by the Doppler signal instrument.

There are several techniques to detect the Doppler frequency shift from transmitted and received ultrasonic signals.

Using phase quadrature detection, A, $A_f$ and $A_r$ represent the amplitudes and $w_c$, $w_f$, $w_r$ represent the radian frequencies of the transmitted, forward-shifted, and reverse-shifted signals, respectively. The received signal can be expressed as $$R = A \cos w_c t + A_f \cos (w_c + w_f)t + A_r \cos (w_c - w_r)t \quad (5)$$

The received signal potentially contains components at the transmitted frequency, $w_c$ (no flow); above the transmitted frequency, $w_c + w_f$ (forward flow); and below the transmitted frequency, $w_c - w_r$ (reverse flow). After demodulation the output signal will be:

$$V_a (-A_f \sin w_f t + A_r \sin w_r t)/2 \quad (6)$$

$$V_b = (A_f \cos w_f t + A_r \cos w_r t)/2 \quad (7)$$

From Eq. (1), assuming a tissue speed of sound of 1540 m/sec, an echo frequency $f_0$ of $5 \times 10^6$ Hz and a 6 reflector velocity V of 0.1 m/sec.:

$$f_D = \frac{2 \times 5 \times 10^6 \text{ cycles/second} \times 0.1 \text{ m/sec}}{1540 \text{ m/sec}} \quad (8)$$

$$f_D = 600 \text{ Hz} \quad (9)$$

The Doppler signal is in the audible frequency range and is recorded on audio tape in 32 for spectral analysis in processor 26. Adequate clinical interpretation can be drawn by analyzing just the Doppler shift signal which contains the information of the blood flow pattern.

When studying the blood flow, the Doppler signal is very complex because of the complicated blood velocity patterns found in most vessels. Usually, the blood velocity is not the same at all points inside the artery, but follows some type of profile, such as a parabolic flow pattern.

Figure 2:
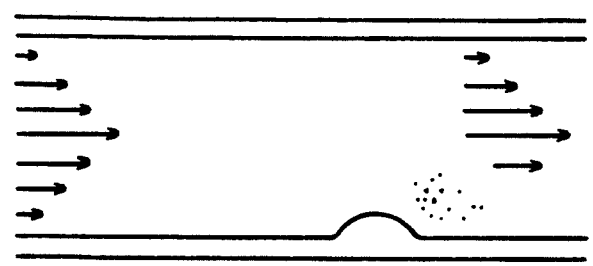
FIG. 2 is a schematic sectional view of an artery having slight cholesterol build up.
Figure 3:
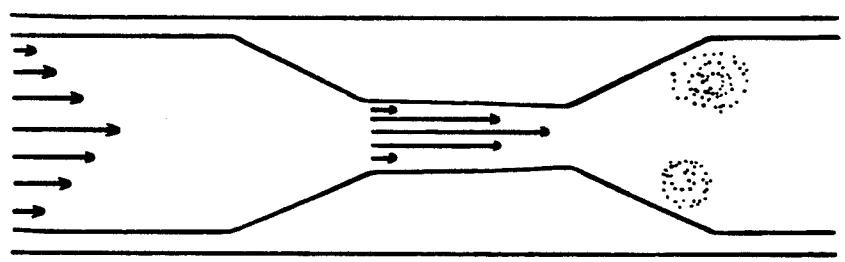
FIG. 3 is a view similar to FIG. 2 showing a seriously stenotic artery.

The actual profile depends on a number of factors, including the size of the vessel, the blood pressure and the presence of obstructions. FIG. 2 illustrates a parabolic flow pattern with a small obstruction in an artery with slight stenosis and FIG. 3 illustrates a flow pattern for an artery with severe stenosis. The arrow vectors show the direction and velocity by their lengths.

If the transducer sound beam and the sampled volume are large compared with the lumen diameter, scattered ultrasound signals will be received simultaneously from blood cells that are moving at different velocities. Flow is normally slowest near the wall because of friction and fastest in the center. The resultant Doppler signal, therefore, will be a composite signal containing many signal-frequency components, each having its own amplitude and phase. Hence, analyzing the power spectrum of this Doppler signal in the frequency domain will give information about the characteristics within the vessel being studied.

Figure 4:
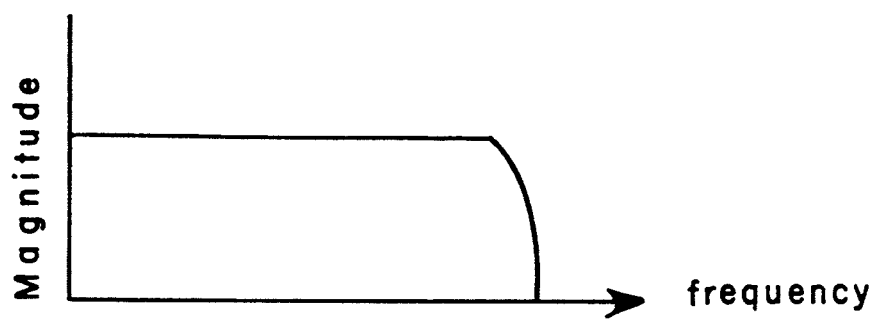
FIGS. 4, 5 and 6 are each graphs plotting, on a relative scale, signal magnitude against frequency for a Doppler signal power spectrum.
Figure 5:
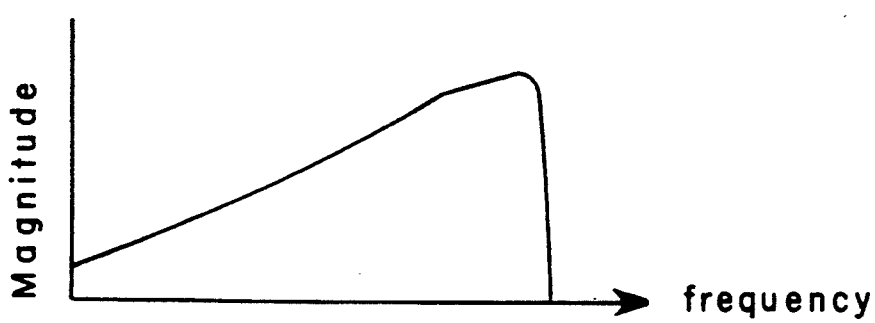
Figure 6:
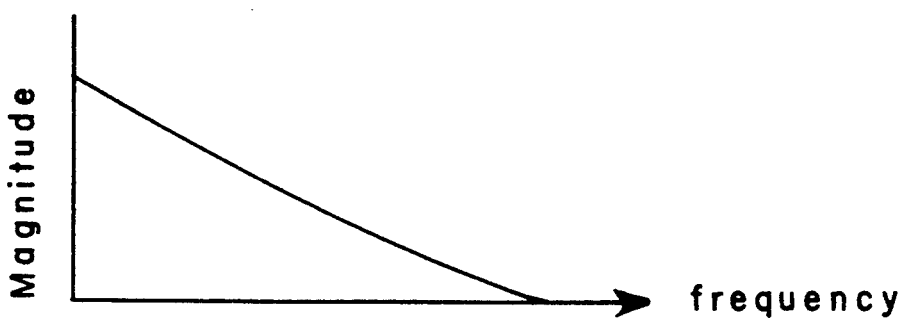

FIG. 4 shows the power spectrum for a vessel having velocities ranging from near zero at the vessel wall through a maximum value, $V_{max}$ at the center of the vessel. The corresponding Doppler signals, having frequencies ranging from nearly zero through the maximum ($f_{max}=2[f_0 v_{max}/c] \times \cos \Theta$) are represented in the power spectrum. As a second example, some larger arteries are known to have blunt flow profiles, that is constant relatively low velocity across the central part of the artery. In these arteries, the frequency spectrum has the appearance shown in FIG. 5. It can be seen that this spectrum is more heavily weighted toward higher frequencies than the previous example because the blood flow in the center is less hindered by the wall friction, thus having faster flow than in the example of FIG. 4. Finally, flow in stenotic (obtruded) regions as shown in FIG. 3, may have a "jet" pattern. If only a small fraction of blood flows with the extremely high velocities of the jet, the resultant Doppler signal power spectrum has the appearance shown in FIG. 6.

The appearance of the Doppler signal spectrum also depends of the size of the sample volume. A pulsed Doppler instrument, with its limited sample volume in the axial direction, will provide a considerably narrowed spectrum than a continuous-wave device.

Another flow pattern that is of considerable interest for the invention is "turbulence" within the vessel. Turbulence, characterized, for example, by shedding or "vortices" and eddies as suggested in FIGS. 2 and 3, may occur ideal to a stenotic region. In that case, the turbulence might result from the very high block velocity present in the narrowed luminal opening caused by stenosis. Thus, when turbulence is present the Doppler signal spectrum will be "broadened" because that higher velocity contributes to higher frequency component in the Doppler signal. "Spectral Broadening" is a very good indication of turbulent flow.

Summarizing, pulse-echo techniques can be used to image the walls of vascular structures, whereas Doppler techniques are used by the invention for detecting and evaluating flow. The Doppler shift frequency is the difference between the frequencies of the transmitted sound beam and the returning echoes. Analysis of the Doppler signal yields important features of the flow patterns inside the artery which helps detect stenosis of the artery.

According to the present invention, the detected Doppler signals are recorded on audio tapes at 32 in FIG. 1, for later analysis in signal processor 26. Analysis in the time domain further facilities understanding and interpretation of the underlying physical process of the signal. The signal is recorded with a frequency cutoff at 3.5 KHz. The data is converted from the soundtrack of a pre-recorded video tape which stores both B-mode images of the conventional Doppler equipment, and the Doppler signals. The data is typically five seconds long, covering approximately 5 to 8 heartbeats depending on each patient's pulse rate.

In a digitation stage of the invention, the data is put through an anti-aliasing filter with cut-off frequency at 4 KHz. Then the data is sampled at 10 KHz to prevent aliasing. The number of quantization levels are 256, thus each sample is quantized to 8 bits (1 byte). The noise introduced at this stage can be approximated according to:

$$SNR = 6n \text{ (dB)} \tag{10}$$

where n is the number of bits. The signal to quantization noise ratio is reasonably large for n=8, so that the digitized data is a good approximation of the original analog waveform.

Figure 7:
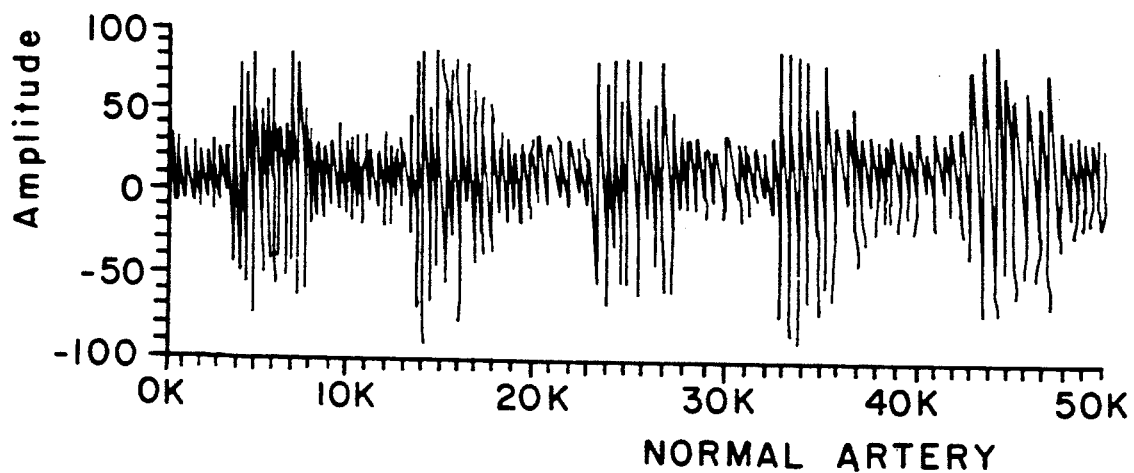
FIGS. 7 and 8 are time domain graphs plotting amplitude against time showing the waveform of a Doppler signal during a five second period, FIG. 7 showing five heartbeats of a normal artery and FIG. 8 showing five heartbeats of a stenotic artery.
Figure 8:
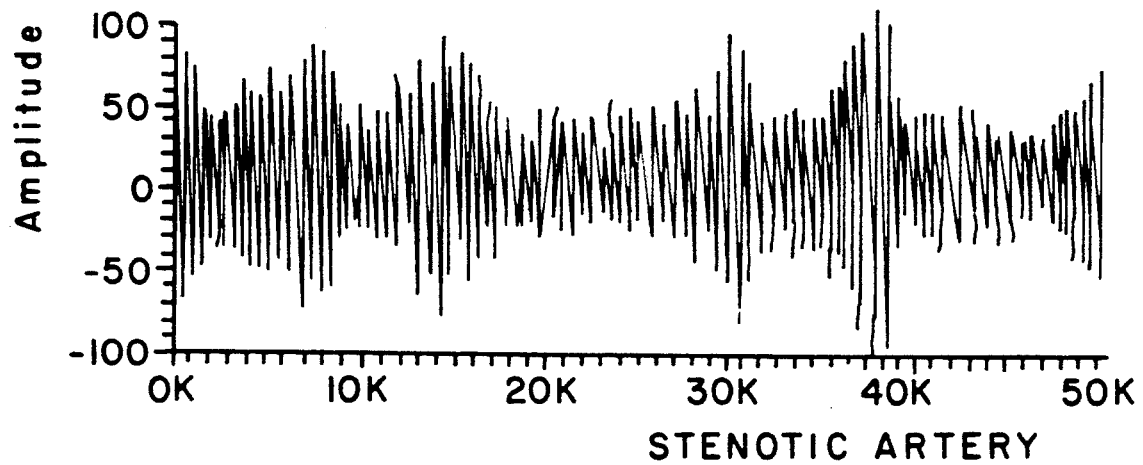

If the Doppler waveform is plotted in the time domain as shown in FIGS. 7 and 8, periodicities caused by the heartbeat are observable about every one second. For a normal artery, FIG. 7, in the systole region, with the heart contracting, energy builds up and is shown by a dense waveform. In diastole, when the heart relaxes, the energy level goes down, resulted in a low amplitude waveform.

In a stenotic artery, FIG. 8, the reduced diameter causes a velocity increase. Distal to stenosis, the increased kinetic energy will be converted back into pressure energy which maintains the flow velocity even when the heart starts to relax. This results in a relatively high energy level in diastole, which is illustrated in FIG. 8 where there is no clear distinction between systole and diastole, unlike the distinctions apparent in FIG. 7.

Figure 9:
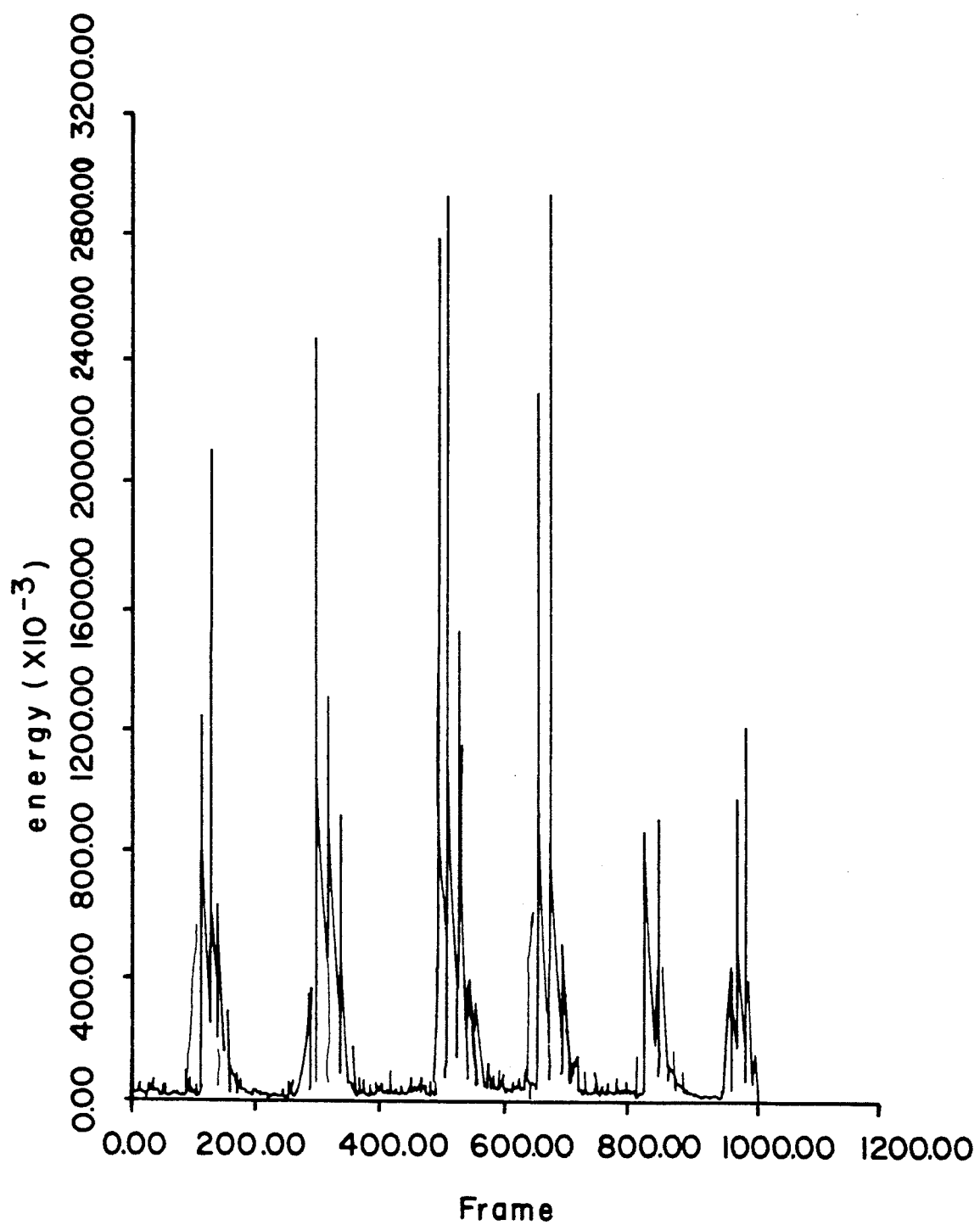
FIG. 9 is a graph plotting energy against time showing an energy contour plot for a normal artery.
Figure 10:
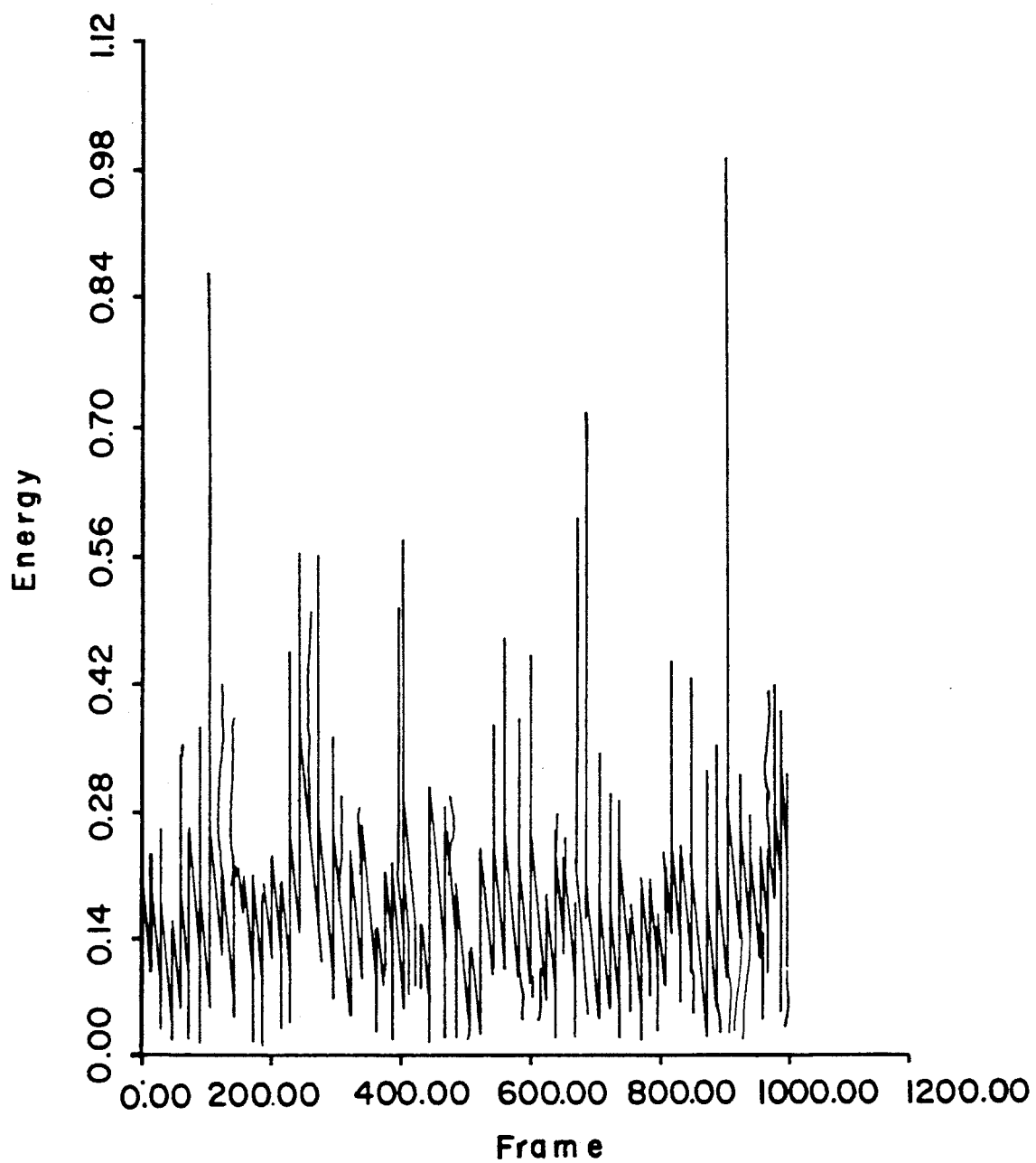
FIG. 10 is a view similar to FIG. 9 for a stenotic artery.

An ever clearer picture is seen from an energy contour as shown in FIGS. 9 and 10. The total energy $E_x$ of a sequence x[n] with length N is defined as $$E_x = \sum_{n=0}^{n=N} f^2(n). \tag{11}$$

The energy contour is a contour that describes the energy variation with respect to time. To achieve this, one first divides the total number of samples N into frames of P samples each. So the number of frames will be N/P. The energy of each frame is calculated according to $$E_x(m) = \sum_{j=1}^{P} f^2(j) \text{ for } m = 1, 2, \ldots N/P. \tag{12}$$

The choice of the frame size P is dependent on the nature of the data. In the data of the invention, the energy contour shows the periodic movement of the rise in systole and fall in diastole. With a sampling rate of 10 KHz and duration of approximately 5 seconds, the total number of samples is 50000. A typical heartbeat rate is approximately 60 beats per minute (or 1 beat per second). There are, therefore, approximately 10000 samples per heartbeat cycle. With a frame size of 50 samples, we will have 200 points in the energy counter plot to represent one period of heartbeat. This is a reasonable choice because it achieves a good tradeoff between resolution and smoothness. Examples of energy contour plots for two patients are shown in FIG. 9 with normal artery, and FIG. 10 with stenotic artery.

Autocorrelation is a technique used to measure how the present samples of a signal are related to the past samples. See the above-identified co-pending patent application. From the autocorrelation sequence we can gain insights into the signal. For example, if the signal is white noise for which the samples at different instants have no correlation, there is a sharply decreasing autocorrelation sequence. Autocorrelation is also a good tool to determine if the signal is periodic and to measure the period. It is not easy to see the periodicity of a periodic signal in the time domain if it is corrupted by noise. But its autocorrelation sequence will still present a periodic sequence with the same period as the time domain signal. Autocorrelations can be used to obtain a power spectral density of the signal according to the invention.

The autocorrelation sequence of an ergodic process is defined as:

$$\sum_{n=0}^{N-m-1} x[n + m]x^*[n] = x[n] \quad x^*[-n] \quad (13)$$

Computationally efficient procedures that perform fast convolutions with FFT algorithms may therefore be used to efficiently compute the discrete autocorrelation estimates. This is one reason why the autocorrelation method is so widely used.

The correlation is a measurement of how two random sequences are statistically related at different points in time. Similarly, autocorrelation of a random sequence measures the degree of correlation between previous samples and later samples of a signal. For a periodic signal with period P samples, it is easy to see that the autocorrelation function of a periodic signal is also periodic with the same period:

$$r_{xx}[m] = r_{xx}[m + P] \quad (14)$$

For a finite length sequence, however, the autocorrelation of a periodic sequence will only be pseudo-cyclic. Since in equation (13) the upper limit of the summation is $N-m-1$, as m increases, the number of terms included in the summation decreases. For a periodic signal, we can still see the periodicity, but the magnitude of each cycle will decrease.

Figure 11:
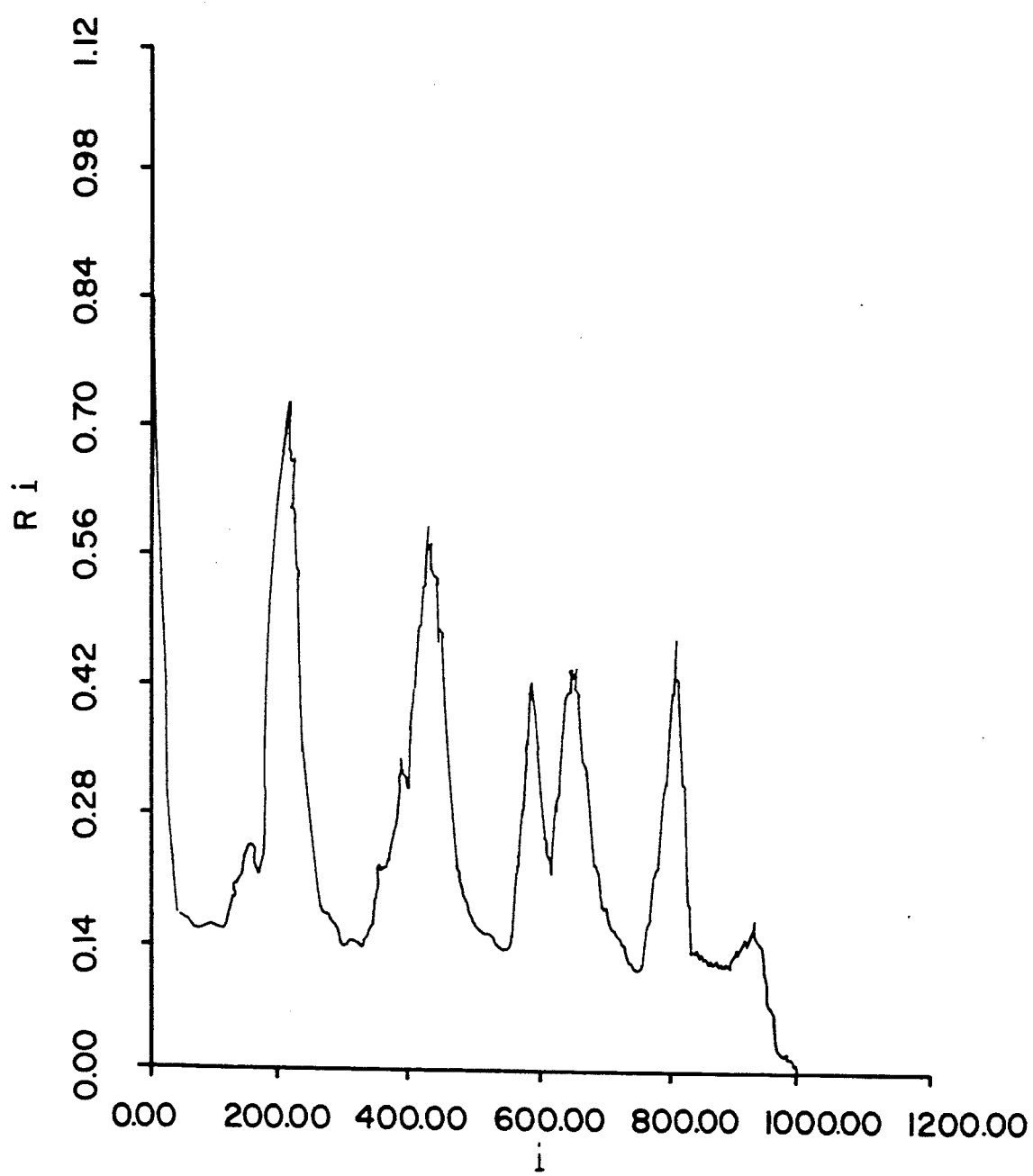
FIG. 11 is a graph plotting autocorrelation of a Doppler signal for an artery without stenosis, in the time domain.
Figure 12:
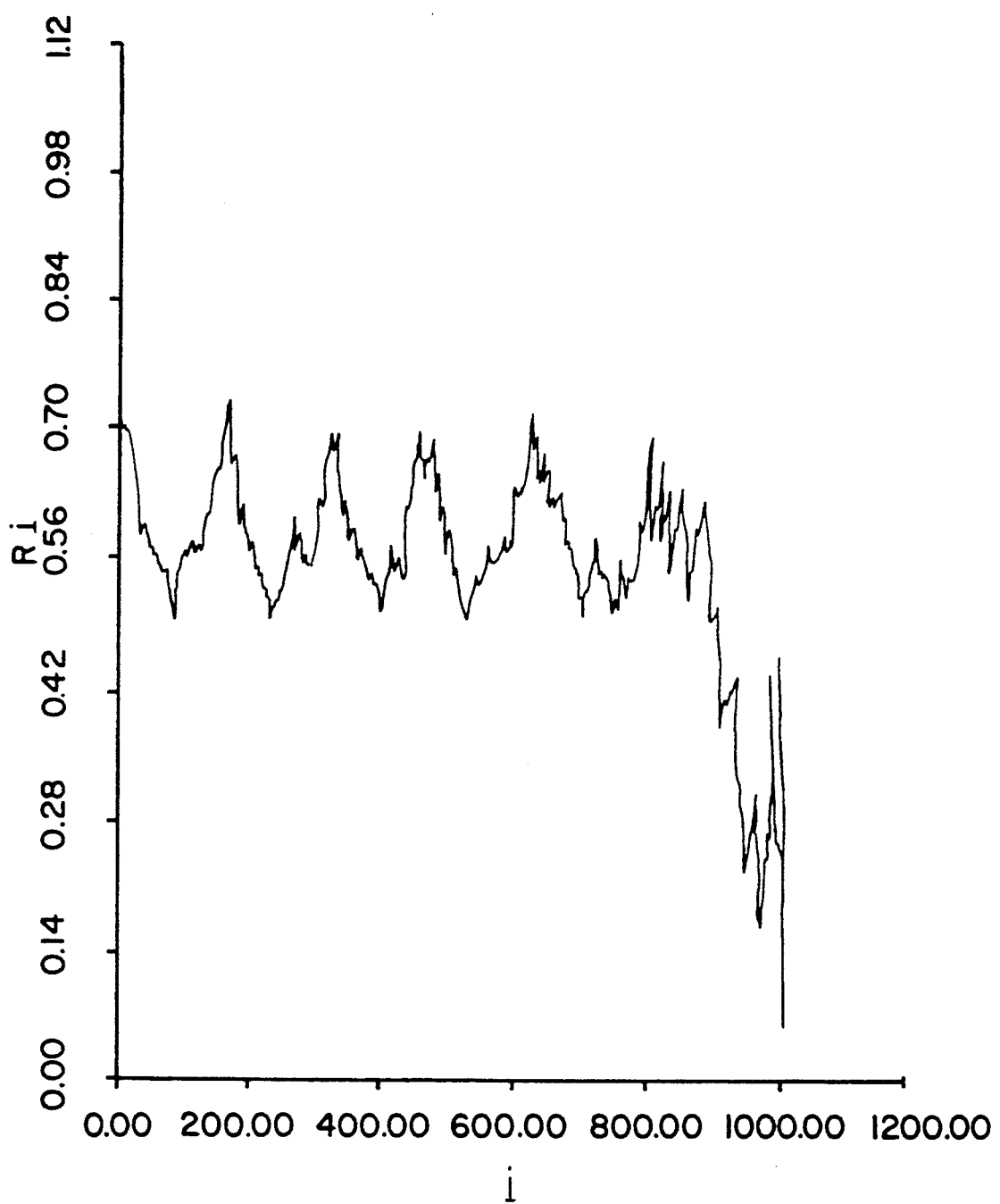
FIG. 12 is a view similar to FIG. 11 for an artery with stenosis.

The Doppler signal being analyzed is periodic with the period of the heartbeat rate. Every period consists of systole and diastole. For data of finite length (5 seconds), autocorrelation is performed according to (13). Two examples are shown in FIGS. 11 and 12. The value of the first valley $r_{xx}[p/2]$ is the correlation of x[n] and the shifted sequence $x[n-p/2]$ where p denotes the period of x[n]. This can be interpreted as the correlation between systole and the following diastole. In arteries that have stenosis, turbulence will result from the very high blood velocity present in the narrowed luminal opening. When the heart starts to contract, the increasing blood velocity causes turbulence in the stenosis region. This turbulence will linger during the diastole even when the heart starts to relax. In other words, the signal in systole and diastole are somewhat correlated in a stenotic artery. In a normal artery (FIG. 11), however, there is only laminal flow since no turbulence exists to "correlate" the systole to the diastole. Thus we can expect to see more correlation between systole and diastole for a stenosis signal (FIG. 12) then for a normal signal.

Although the Doppler signal of the blood flow inside the artery has the inherent periodicity of the heartbeat, two heartbeat cycles will never produce exactly the same energy, blood volume, flow pattern, etc. That means the signal is not strictly periodic. From a stochastic approach, the Doppler signal belongs to the class of stochastic processes called: cyclostationary processes.

The power spectral density (PSD) is defined as the Discrete Fourier Transform of the autocorrelation sequence R(r). This means that PSD is only valid for a stationary process. In the frequency domain, stationary signals will have the same frequency spectrum at any instant in time. For a non-stationary signal, the spectrum changes from instant to instant. For the Doppler signal, we already know it is proportional to the blood velocity inside the artery "sample volume" (Eq. (1)). The blood velocity is changing from instant to instant, depending on whether the beat is in systole or diastole. During systole, the velocity is increasing whereas during diastole the velocity decreases. Thus the Doppler shift, $f_D$, is also changing from time to time The Doppler signal is thus non-stationary. Since the data is non-stationary, a simple Fourier transform will not yield any insight into the signal. However, if we divide the data into small frames of short length, such that the statistics of the data do not change much within the frame, we can obtain the PSD of the frames. This is called Short-time Fourier Analysis.

Assuming short-time stationarity, the selection of length of the time window during which to perform the analysis is important. This length affects the frequency resolution. In the inventive case, the window length will have to be small (less that 5 milliseconds) in order for the short time stationarity condition to be valid. With a sampling rate of 10 KHz (resulting in 10 samples/msec), the analysis window includes only 10 samples. This time is short enough to retain the stationarity. But to see the spectrum range of 5 KHz which is half the sampling rate, the resulting resolution is only $$5 \text{ KHz}/10 \text{ samples} = 500 \text{ Hz/sample} \quad (15)$$

That is very poor resolution. To achieve a reasonably good trade-off between resolution and stationarity, according to the invention the window size of 5 milliseconds is used, which will contain 50 samples. This will allow a resolution of 100 Hz. This is reasonable for a maximum frequency of 5 KHz which is the case in the present application.

As noted above, "spectrum broadening" is one indication of the presence of stenosis. Because of the importance of spectral analysis in diagnosing stenosis and many other studies of arterial physiology, various analytical approaches have been developed to display the data as a full spectrum of frequencies simultaneously, and thus preserve their true time-varying multi-frequency component character. The most important one among them is the Fast-Fourier Transform (FFT) of small windowed data that allows the representation of frequency versus time versus intensity.

Because of the contractility between maintaining stationarity within a frame and resolution of the spectrum, the short-time Fourier transform can only serve as a qualitative explanation tool. The invention cannot use this directly as a feature for classification.

Observing that the Doppler signal is a periodic stochastic signal, the periodic stochastic signal is not defined in a formal way. A process x(t) is called cyclostationary (or periodically stationary) if its statistics are invariant to a shift of the time origin by integral multiples of a constant T (period). A process x(t) is called wide-sense (W.S.) cyclostationary if $$\eta(t+mT) = \eta(t). \qquad (16)$$

and $$R(t+mT+\tau, t+mT) = R(t+\tau, t). \qquad (17)$$

In our Doppler signal, if we take the heartbeat period to be T, it is not hard to see that our x[n] satisfied equation (16) and (17). In the frequency domain, cyclostationary will mean that the short-time spectrum will repeat in every period T. This is under the assumption that the heart beats evenly during the time of ultrasonic Doppler testing, which is usually true under laboratory testing conditions. This cyclostationarity can also be understood from the time domain periodicity in FIGS. 7 and 8.

Two stage stationarity is similar to the theory of cyclostationarity. The heart contracts and relaxes periodically causing the velocity of the blood flow to change from time to time. This is the main reason for the non-stationarity of data. However, during every heartbeat, there are only two main different stages: systole and diastole. If we only deal with the systole or the diastole, the statistics of the data should be reasonably close within one stage. In the frequency domain, the short-time spectrum should have a certain resemblance. We thus call it "two stage stationarity". This "two stage stationarity" assumption serves as the algorithms for feature extraction and classification that will be discussed later.

Figure 13:
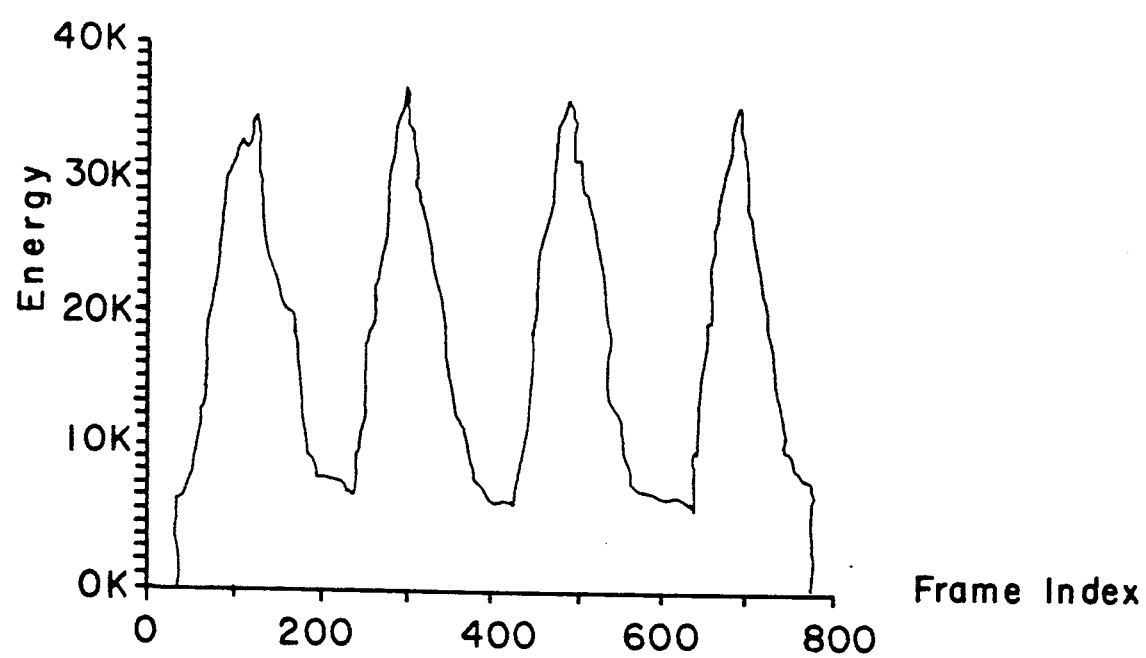
FIG. 13 is a graph plotting energy against frame index for separation of systole from diastole phases of heartbeats.

The separation of stage has some resemblance to the problem of removing the silence from the actual speech signal in speech preprocessing. But the latter case is a problem of locating the exact beginning and end of a speech utterance in a background noise. The regions that correspond to each word has to be located to a certain degree of precision. While in the Doppler signal of the invention, the exact beginning and ending of the systole or diastole is not important. From FIG. 13, if we set the average energy level as the threshold, we can get the approximate separation between systole and diastole. Since the exact starting and ending points are not important to make sure that the diastole part being extracted is pure, we can throw away the marginal data by lowering the energy threshold.

With a sampling frequency of 10 KHz and heartbeat rate of one every second, one period will consist of 10 K samples. For a frame of 50 samples each, we will have 200 frames for every one second of recording. Taking away the transition from systole to diastole and diastole to systole will at most account for one quarter of the total number of frames (200 frames). The resulting number of frames of systole or diastole is at least 150 frames. Taking half of that as the diastole stage, we will have approximately 75 frames in one second.

Power spectral density (PSD) is defined as the discrete-time Fourier transform of an infinite autocorrelation sequence (ACS). This transform relationship between the PSD and ACS may be considered to be a non-parametric description of the second-order statistic of the random process. The PSD of the time series model is a function of the model parameters rather than the ACS. The most widely used models are the autoregressive (AR) process, the moving average process (MA), and the autoregressive moving average (ARMA). See the above-identified co-pending application for additional information on ARMA.

The parametric models of the invention have the ability to achieve better and faster PSD estimation than by non-parametric methods, such as FFT.

The AR model is the most widely used in speech analysis and the AR parameters are often called linear predictive coefficients (LPC). In this invention the terms LPC and AR refer to the same model.

As noted above, the Doppler signal is a non-stationary process. Accordingly, predictor coefficients for LPC analysis are done on a frame by frame basis.

The computations involved in solving for the LPC coefficients are more complicated than for the autocorrelation method. A comparison of the frequency response, with parameters dependent on different persons, and different stages in a heartbeat cycle. The driving force of the heartbeat in systole is one form of excitation. More importantly, in diastole, the heart relaxes and no deterministic driving force is present in the artery. Thus an excitation to a filter for stenotic diagnosis uses the signal driving diastole as a white noise sequence.

The final purpose is to recognize from the Doppler signal, whether an artery has stenosis or not. We can do this by looking at the diastolic portion of the signal only. In the proposed model the input was assumed to be white Gaussian noise. Analyzing the spectral density of the output of this model will be equivalent to analyzing the filter response. Thus, we have established a complete analogy between the speech production model and the Doppler signal production model. The LPC analysis and cepstrum analysis of the invention follows.

During the diastolic period of the LPC model for the Doppler signal of the blood flow inside an artery, a spectral density function X(z) can be approximated by H(z), which is an all pole filter with parameters $a_k$ for k=1, 2..., p. Further, the presence of stenosis will change the blood flow pattern inside the artery. This flow pattern is directly reflected by the Doppler signal in the spectral display. A simple example noted above, is that the presence of stenosis is likely to cause the "spectral broadening" in the spectral domain because of the increased blood flow speed and the resulting turbulence. Accordingly, the set of LPC coefficients is a good feature to differentiate stenosis from a normal signal. However, in the feature space, in order to classify the features extracted from different Doppler signals, certain kinds of distance measures are needed. One expects that the features from within a class cluster together while those extracted from different classes be as far apart as possible.

While Euclidean space is the most common space in which one can measure the length of vectors and distance between point, LPC coefficients are not Euclidean distance measurable.

Bayes decision rule for minimizing the probability of error is:

Decide $\omega_0$ if $P(\omega_0|\vec{x}) \geq P(\omega_1|\vec{x})$;

otherwise decide $\omega_1$.

If we define $$g_i(\vec{x}) = \log P(\omega_1/\vec{x}) \qquad (18)$$

where $\vec{g}(x)$ is called "discriminant function", then the Bayes classifier can be represented as:

Assign a feature vector $\vec{x}$ to class $w_i$ if $$g_j(\vec{x}) \leq g_i(\vec{x}) \text{ for all } j \neq i. \qquad (19)$$

For our two class classification problem, we can further write the discriminate function as $$g(\vec{x}) = g_0(\vec{x}) - g_1(\vec{x}), \qquad (20)$$

As introduced earlier, first separate the diastolic from the systolic data, then segment the diastolic data into frames. As a result:

(1) Those diastolic frames should have approximately the same statistics and (2) They contain the useful information about whether the signal is from stenotic artery or not.

Samples for the invention are all from the diastolic portion of the data. And we will also assume that the features vectors (LPC cepstrum) are Gaussian distributed. Statistics shows that when using a large set of data, the LPC cepstrum will converge to a Gaussian distribution.

Let $\vec{x}_{ij}(k)$ be an N-dimensional feature vector derived from the kth frame during the analysis of patient j who belongs to class $w_i$. Also let $c_i$ be the number of patients (pattern class) in the training population in class $w_i$, for $i=0,1$. Notice that the frame index k refers only to frames in the diastolic part of the heartbeat, so it is not continuous.

$M_{ij}$ is the total number of frames that a jth patient contributed to the training. The total number of training vectors for class i then is $$\sum_{j=1}^{c_i} M_{ij},$$

denoted as $NT_i$. The "training" in this quadratic classifier actually means the estimation of the mean and covariance of the feature vectors from each class.

The means vector $\vec{\mu}_i$ and covariance matrix $\Sigma_i$ for $i=0, 1$ are defined as $$\vec{\mu}_i = E\{\vec{x}_{ij}(k)\}, \qquad (21)$$

and $$\Sigma_i = E\{(\vec{x}_{ij}(k) - \vec{\mu}_i)(\vec{x}_{ij}(k) - \vec{\mu}_i)^T\}. \qquad (22)$$

and are computed according to $$\vec{\mu}_i = \frac{1}{NT_i} \sum_{j=1}^{c_i} \sum_k \vec{x}_{ij}(k), \qquad (23)$$

$$\Sigma_i = \frac{1}{NT_i - 1} \sum_{j=1}^{c_i} \sum_k [(\vec{x}_{ij}(k) - \vec{\mu}_i)(\vec{x}_{ij}(k) - \vec{\mu}_i)^T]. \qquad (24)$$

where the sum over k contains a total of $M_{ij}$ feature vectors, and k is the selected frame number index f1, f2, f3, etc.

In the first phase of the training stage, the parameters $\vec{\mu}_i$ and $\Sigma_i$ for observations $\vec{x}_{ij}(k)$ are estimated, where $i=0$ or $i=1$ is the known class label. Now in the classification stage, a score $g(\vec{x})$ is obtained. Plotting the score for all the $NT_1 + NT_0$ vectors sets a threshold level where the two curves intersect. For this reason, this classifier is also called a threshold classifier.

A feature is assigned to class zero ($w_0$) when $g(\vec{x})$ is greater than 0 and to class $w_i$ when it is less than zero. This means that the natural threshold is at zero.

Since we do not know the probability density function $p(w_i|\vec{x}$, we assume it is Gaussian distributed and estimate the parameters of the distribution, the mean and the covariance matrix, $\vec{\mu}_i$ and $\Sigma_i$. The estimation error of the means $\vec{\mu}_i$, will be accumulated through the estimation the covariance matrix, causing more bias to the estimated $\vec{\Sigma}_i$. This directly caused the bias of the constant term $\log |\Sigma_i|$ thus shifting the threshold away from zero.

Fortunately, this will not cause any problem in classification. All we have to do is to plot the distribution of the likelihood ratio of the two classes and modify the decision rule to be Decide $\omega_0$, if $g_0(\vec{x}) \geq g_1(\vec{x})$; \qquad (25)

Decide $\omega_1$, otherwise. \qquad (26)

If we denote the point where $$g(\vec{x}|\omega_0) = g(\vec{x}/|\omega_1) \qquad (27)$$

as $g_0$, then it is easily seen that if we shift the original to $g_0$, our modified decision rule is equivalent to the original one in Eq. (20). Notice that if we shift the origin to $g_0$ in training, we should do the same operation to the testing set to maintain consistency.

The present invention thus subjects a digital signal derived from the acoustic signal, preferably a Doppler signal, to pattern recognition analysis that is systematic and comprise the steps of selecting features which are dominant for stenosis and which are multidimensional in a feature space, projecting the multi-dimensional features in the best directions, for example to enhance clustering of the feature, followed by classification to determine whether stenosis exists or not.

Examples of feature selection include simultaneous time and frequency analysis of the Doppler signal using a transform such as a Winger or Exponentional Distribution. Feature selection may also include autoregressive analysis of the Doppler signal, where the Doppler signal has systolic and diastolic portions, the method including using a white noise frequency filter in the autoregressive analysis corresponding to the diastolic portion of the Doppler signal. The autocorrelation analysis may use one of PARCOR, log-area and cepstral coefficients.

Examples of suitable projection of the feature space is the plotting of a power spectrum of the Doppler signal in the frequency domain, or plotting an energy contour of the Doppler signal in the time domain over a plurality of heartbeats, or plotting a waveform of the Doppler signal in the time domain over a plurality of heartbeats, or autocorrelating the Doppler signal in the time domain over a plurality of heartbeats. An example of classification is analyzing the power spectrum in the frequency domain to determine whether it is weighted toward a low frequency end which would indicate the presents of stenosis. Another example is the broadening of the power spectrum in the frequency domain which would also indicate stenosis. If the energy contour of the Doppler signal from the time domain has a low distribution between systolic and diastolic phases, this also indicates stenosis. Stenosis is also indicated by analyzing whether the waveform which is plotted in the time domain, has a low distinction between the systolic and diastolic phases of the heartbeat. Further, an autocorrelation of an artery which stenosis which has shallow valleys between systolic and diastolic phases of the heartbeats also indicates stenosis.

While the specific embodiments of the invention have been shown and described in detail to illustrate the application of the principles of the invention, it will be understood that the invention may be embodied otherwise without departing from such principles.

What is claimed is:

1. A method of diagnosing arterial stenosis comprising:

detecting an acoustic signal from an artery;

digitizing the acoustic signal to form a digital signal on which computational analysis can be performed; and subjecting the digital signal to pattern recognition analysis to distinguish digital signals of an artery with stenosis from digital signals of a normal artery;

the digital signal containing a plurality of features each in a multidimensional feature space, the pattern recognition analysis comprising the steps of:

selecting features which are dominant for stenosis, from the digital signal;

projecting each selected featured in its multidimensional feature space into a selected direction for increasing discrimination between digital signals of arteries having stenosis and digital signal of arteries without stenosis; and classifying the projected features to discriminate between projected features of arteries having stenosis from projected features of arteries without stenosis.

2. A method according to claim 1, including directing an ultrasonic signal toward an artery to be diagnosed, detecting an ultrasonic echo from the artery, the echo being the acoustic signal, and subjecting the echo to Doppler analysis to form a Doppler signal.

3. A method according to claim 2, wherein the projection step of the pattern recognition analysis includes plotting a power spectrum of the Doppler signal in the frequency domain, and analyzing whether the power spectrum is weighted toward a low frequency end of the spectrum to indicate stenosis.

4. A method according to claim 2, wherein the projection step of the pattern recognition analysis includes plotting a power spectrum of the Doppler signal in the frequency domain, and analyzing whether the power spectrum is broadened to indicate stenosis.

5. A method according to claim 2, wherein the projection step of the pattern recognition analysis includes plotting an energy contour of the Doppler signal in the time domain over a plurality of heartbeats each having systolic and diastolic phases, and analyzing whether the energy contour has low distinction between systolic and diastolic phases to indicate stenosis.

6. A method according to claim 2, wherein the projection step of the pattern recognition analysis includes plotting a waveform of the Doppler signal in the time domain over a plurality of heartbeats, and analyzing whether the waveform has low distinction between systolic and diastolic phases of the heartbeats to indicate stenosis.

7. A method according to claim 2, wherein the projection step of the pattern recognition analysis includes autocorrelating the Doppler signal in the time domain over a plurality of heartbeats, and analyzing whether the autocorrelation of an artery with stenosis has shallow valleys between systolic and diastolic phases of the heartbeats, to indicate stenosis.

8. A method according to claim 2, wherein the pattern recognition analysis includes simultaneous time and frequency analysis of the Doppler signal using a transform.

9. A method according to claim 8, wherein the transform is a Wigner or Exponential Distribution.

10. A method according to claim 2, wherein the pattern recognition analysis includes autoregressive analysis of the Doppler signal.

11. A method according to claim 10, wherein the autoregressive analysis includes autoregressive-moving average analysis using linear predictive coefficients (LPC).

12. A method according to claim 10, wherein the Doppler signal has systolic and diastolic portions, the method including using a white noise frequency filter in the autoregressive analysis corresponding to the diastolic portions of the Doppler signal.

13. A method according to claim 10, wherein the autoregressive analysis includes linear predictive coefficient cepstrum analysis for identifying feature vectors that indicate stenosis.

14. A method according to claim 1, wherein the auto correlation analysis uses one of a PARCOR, log-area and cepstral coefficients.

* * * * *